United States Patent
Tsubokura et al.

(10) Patent No.: US 9,233,849 B2
(45) Date of Patent: *Jan. 12, 2016

(54) PROCESS FOR PRODUCING FLUORINE-CONTAINING SULFONYLIMIDE SALT

(75) Inventors: Shiro Tsubokura, Takaoka (JP); Toru Suzuki, Myoko (JP); Michiaki Maruyama, Myoko (JP); Yasuyuki Aiura, Myoko (JP)

(73) Assignee: NIPPON SODA CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/985,915

(22) PCT Filed: Feb. 28, 2012

(86) PCT No.: PCT/JP2012/054888
§ 371 (c)(1),
(2), (4) Date: Aug. 16, 2013

(87) PCT Pub. No.: WO2012/118063
PCT Pub. Date: Sep. 7, 2012

(65) Prior Publication Data
US 2013/0323155 A1 Dec. 5, 2013

(30) Foreign Application Priority Data
Mar. 3, 2011 (JP) ................. 2011-046739

(51) Int. Cl.
*C07C 303/40* (2006.01)
*C01B 21/087* (2006.01)
*C01B 21/093* (2006.01)
*C01B 21/086* (2006.01)

(52) U.S. Cl.
CPC ............. *C01B 21/086* (2013.01); *C01B 21/087* (2013.01); *C01B 21/093* (2013.01); *C07C 303/40* (2013.01)

(58) Field of Classification Search
CPC .. C07C 303/40; C07C 311/48; C07C 209/00; C01B 21/086; C01B 21/087; C01B 21/093; C01B 21/092; H01M 10/0568; H01M 8/1048
USPC ........................................... 423/386; 564/296
See application file for complete search history.

(56) References Cited

U.S. PATENT DOCUMENTS

| | | | |
|---|---|---|---|
| 3,882,128 A | 5/1975 | McLaren et al. | |
| 4,374,818 A | 2/1983 | Rieck | |
| 5,916,475 A | 6/1999 | Michot et al. | |
| 6,107,493 A * | 8/2000 | Pohl et al. | 548/952 |
| 6,365,301 B1 | 4/2002 | Michot et al. | |
| 2009/0292105 A1 | 11/2009 | Michot | |
| 2010/0137609 A1 | 6/2010 | Iwaya | |

FOREIGN PATENT DOCUMENTS

| | | | |
|---|---|---|---|
| CN | 1469845 A | 1/2004 | |
| CN | 101503382 A | 8/2009 | |
| CN | 101778835 A | 7/2010 | |
| EP | 2 476 666 A1 | 7/2012 | |
| JP | A 57-95813 | 6/1982 | |
| JP | A 8-511274 | 11/1996 | |
| JP | A 2000-506132 | 5/2000 | |
| JP | 2001-527505 A | 12/2001 | |
| JP | 2009-292728 A | 12/2009 | |
| JP | 2010-168308 A | 8/2010 | |
| JP | A 2010-168249 | 8/2010 | |
| JP | A 2010-189372 | 9/2010 | |
| SG | 192258 A1 | 9/2013 | |
| WO | WO 97/31909 A1 | 9/1997 | |
| WO | WO2009123328 | * 10/2009 | ............ C01B 21/086 |
| WO | 2010/010613 A1 | 1/2010 | |

OTHER PUBLICATIONS

Vacuubrand (pdf of <http://www.vacuubrand.com/us/page823.html, downloaded on May 28, 2015.*
Mar. 27, 2012 Search Report issued in International Patent Application No. PCT/JP2012/054888 (with translation).
Feb. 20, 2014 Office Action issued in Taiwanese Patent Application No. 101106685 (with partial translation).
Nov. 18, 2014 Supplementary European Search Report issued in European Application No. 12752499.9.
Jul. 31, 2014 Office Action issued in Chinese Patent Application No. 201280010507.4 (with translation).
Appel et al., "Über die Reaktion von Sulfuryl-di-isocyanat mit Halogeno-schwefelsäuren. Ein einfaches Verfahren zur Herstellung von Flour-sulfonylisocyanat und Imido-bis-schwefelsäurefluorid," Chemische Berichte, 1964, vol. 97, pp. 849-850.
Beran et al., "A New Method of the preparation of Imido-bis(sulfuric acid) Dihalogenide, (F,Cl), and the Potassium Salt of Imido-bis-(sulfuric acid) Difluoride," Z. Anorg. Allg. Chem., 2005, vol. 631, pp. 55-59.
Ruff et al., "Imidodisulfuryl Fluoride, Cesium Imidodisulfuryl Fluoride, and Fluoroimidodisulfuryl Fluoride," Inorganic Synthesis, 1968, vol. 11, pp. 138-140.
Apr. 4, 2014 Office Action issued in Taiwanese Application No. 101103174.

(Continued)

*Primary Examiner* — Jafar Parsa
*Assistant Examiner* — Amy C Bonaparte
(74) *Attorney, Agent, or Firm* — Oliff PLC

(57) ABSTRACT

By reacting a fluorine-containing sulfonylimide ammonium salt such as ammonium N,N-di(fluorosulfonyl)imide with an alkali metal hydroxide such as lithium hydroxide, potassium hydroxide or sodium hydroxide under reduced pressure and at a low temperature of approximately 40° C., a fluorine-containing sulfonylimide alkali metal salt such as lithium N,N-di(fluorosulfonyl)imide, potassium N,N-di(fluorosulfonyl)imide or sodium N,N-di(fluorosulfonyl)imide is obtained.

2 Claims, No Drawings

(56) References Cited

OTHER PUBLICATIONS

Appel et al., "Über die Reaktion von Sulfuryl-di-isocyanat mit Halogeno-schwefelsäuren. Ein einfaches Verfahren zur Herstellung von Fluor-sulfonylisocyanant und Imido-bis-schwefelsäurefluorid," Chemische Berichte, 1964, vol. 97, pp. 849-850.

Beran et al., "A New Method of the Preperation of Imido-bis(sulfuric acid) Dihalogenide, (F, Cl), and the Potassium Salt of Imido-bis-(sulfuric acid) Difluoride," Z. Anorg. Allg. Chem., 2005, vol. 631, pp. 55-59.

Han et al., "Lithium bis(fluorosulfonyl)imide (LiFSI) as Conducting Salt for Nonaqueous Liquid Electrolytes for Lithium-ion batteries: Physicochemical and Electrochemical Properties," Journal of Power Sources, vol. 196, pp. 3623-3632, 2011.

Krumm et al., "Synthesis of Poly- and the First Perfluoroalkyl-N(SO2F)2 Derivatives: Improved Methods for the Preparation of XN(SO2F)2 (X=H, Cl) and Single-Crystal Diffraction Studies of HN(SO2Cl)2, HN(SO2F)2, and CF3CH2N(SO2F)2," Inorg. Chem., 1998, vol. 37, pp. 6295-6303.

Paul et al., "Chemistry of Imidobis(Sulphuryl Chloride)-III, Solvolytic Reactions and the Nature of the Solvolysed Products," J. Inorg. Nucl. Chem., vol. 40, pp. 2001-2003, 1978.

Ruff et al., "Imidodisulfuryl Flouride, Cesium Imidodisulfuryl Fluoride, and Fluoroimidodisulfuryl Fluoride," Inorganic Synthesis, 1968, vol. 11, pp. 138-140.

Ruzicka et al., "Zur Synthese von Ammonium-imido-bis(schwefelsäura-fluorid) NH4N(SO2F)2," Z. Chem., 1987, vol. 27, No. 6, pp. 227-228.

May 23, 2014 Supplementary European Search Report issued in European Application No. 12752317.3.

Feb. 28, 2012 International Search Report issued in International Application No. PCT/JP2012/051952.

May 29, 2012 International Search Report issued in International Application No. PCT/JP2012/054566.

Jun. 21, 2013 Office Action issued in Taiwanese Application No. 101103174.

Jul. 16, 2014 Office Action issued in Singapore Application No. 2013057930.

Aug. 15, 2014 Office Action issued in U.S. Appl. No. 14/001,547.

Mar. 11, 2015 Office Action issued in U.S. Appl. No. 14/001,547.

Jun. 3, 2015 Notice of Allowance issued in U.S. Appl. No. 14/001,547.

Jul. 13, 2015 Notice of Allowance issued in U.S. Appl. No. 13/984,069.

May 29, 2012 Written Opinion issued in International Application No. PCT/JP2012/054566.

\* cited by examiner

PROCESS FOR PRODUCING FLUORINE-CONTAINING SULFONYLIMIDE SALT

TECHNICAL FIELD

The present invention relates to a process for producing a fluorine-containing sulfonylimide salt. More specifically, the present invention relates to a process for efficiently producing a fluorine-containing sulfonylimide alkali metal salt or a fluorine-containing sulfonylimide onium salt (excluding the ammonium salt) from a fluorine-containing sulfonylimide ammonium salt.

Priority is claimed on Japanese Patent Application No. 2011-046739, filed Mar. 3, 2011, the content of which is incorporated herein by reference.

BACKGROUND ART

Fluorine-containing sulfonylimide salts are useful compounds in a wide variety of fields, and are used as electrolytes, as additives added to the electrolytes of fuel cells, and as selective electron withdrawing materials and the like (see Patent Document 1).

Various processes have been proposed for synthesizing fluorine-containing sulfonylimide salts. For example, Patent Document 2 proposes a process for producing a fluorine-containing sulfonylimide salt by reacting a fluorine-containing sulfonylimide onium salt with an alkali metal compound. Specifically, in Patent Document 2, triethylammonium N-(fluorosulfonyl)-N-(trifluoromethylsulfonyl)imide and an aqueous solution prepared by dissolving lithium hydroxide monohydrate are mixed together under normal pressure, and the solvent is then distilled to dryness to obtain lithium N-(fluorosulfonyl)-N-(trifluoromethylsulfonyl)imide.

Further Patent Document 3 discloses that by adding a tetrahydrofuran solution of lithium hydroxide monohydrate to a tetrahydrofuran solution of an ammonium cyclo-perfluoroalkane-1,n-bis[sulfonyl]imide, and then boiling for 120 minutes, a lithium cyclo-perfluoroalkane-1,n-bis[sulfonyl]imide is obtained.

DOCUMENTS OF RELATED ART

Patent Documents

Patent Document 1: Published Japanese Translation No. Hei 08-511274 of PCT
Patent Document 2: Japanese Unexamined Patent Application, First Publication No. 2010-168249
Patent Document 3: Published Japanese Translation No. 2000-506132 of PCT

DISCLOSURE OF INVENTION

Problems to be Solved by the Invention

In the processes disclosed in Patent Documents 2 and 3, sometimes the cation exchange reaction between the fluorine-containing sulfonylimide ammonium salt and the alkali metal salt does not proceed efficiently.

Accordingly, an object of the present invention is to provide a process for efficiently producing a fluorine-containing sulfonylimide alkali metal salt or a fluorine-containing sulfonylimide onium salt (excluding the ammonium salt) from a fluorine-containing sulfonylimide ammonium salt.

Means to Solve the Problems

The inventors of the present invention undertook intensive investigations in order to achieve the above object. As a result they discovered that by subjecting a fluorine-containing sulfonylimide ammonium salt to a cation exchange reaction under conditions of low temperature and reduced pressure, using at least one compound selected from the group consisting of metal hydroxides and onium hydroxides, a fluorine-containing sulfonylimide metal salt or fluorine-containing sulfonylimide onium salt (excluding the ammonium salt) could be produced with good efficiency. The present invention was completed on the basis of these findings.

In other words, the present invention provides the following.

(1) A process for producing a fluorine-containing sulfonylimide salt represented by formula [II] (hereafter also referred to as "compound [II]"), the process including subjecting a fluorine-containing sulfonylimide ammonium salt represented by formula [I] (hereafter also referred to as "compound [I]") to a cation exchange reaction under reduced pressure, using at least one compound selected from the group consisting of metal hydroxides and onium hydroxides.

(2) The process for producing a fluorine-containing sulfonylimide salt disclosed above in (1), wherein the at least one compound is selected from the group consisting of alkali metal hydroxides and onium hydroxides.

[Chemical Formula 1]

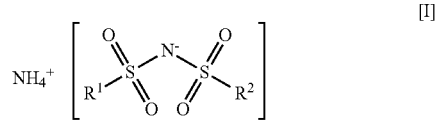

In formula [I], each of $R^1$ and $R^2$ independently represents a fluoroalkyl group having 1 to 6 carbon atoms, or a fluorine atom. $R^1$ and $R^2$ may be bonded to each other to form a ring.

[Chemical Formula 2]

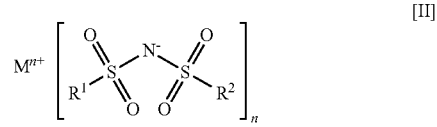

In formula [II], $M^{n+}$ represents a metal cation or an onium cation (excluding $NH_4^+$), n corresponds with the valency of the metal cation or the onium cation (excluding $NH_4^+$) and is an integer of 1 to 4, and $R^1$ and $R^2$ are the same as defined above in formula [I]. $R^1$ and $R^2$ may be bonded to each other to form a ring.

Effects of the Invention

According to the present invention, a fluorine-containing sulfonylimide metal salt or a fluorine-containing sulfonylimide onium salt (excluding the ammonium salt) can be produced from a fluorine-containing sulfonylimide ammonium salt in an industrially efficient manner.

EMBODIMENTS OF THE INVENTION (Process for Producing Compound [II])

The process for producing a compound [II] according to the present invention includes the step of subjecting a compound [I] to a cation exchange reaction under reduced pressure, using at least one compound selected from the group consisting of metal hydroxides and onium hydroxides. The at least one compound is preferably selected from the group consisting of alkali metal hydroxides and onium hydroxides, and is more preferably an alkali metal hydroxide.

The compound [I] used in the present invention is a compound represented by formula [I].

[Chemical Formula 3]

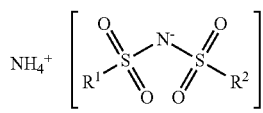

[I]

In formula [I], each of $R^1$ and $R^2$ independently represents a fluoroalkyl group having 1 to 6 carbon atoms, or a fluorine atom. $R^1$ and $R^2$ may be bonded to each other to form a ring. $R^1$ and $R^2$ are preferably fluorine atoms.

The number of carbon atoms constituting the fluoroalkyl group for $R^1$ and $R^2$ is from 1 to 6, preferably from 1 to 4, and more preferably from 1 to 2. Examples of the fluoroalkyl group include a fluoromethyl group, difluoromethyl group, trifluoromethyl group, fluoroethyl group, difluoroethyl group, 2,2,2-trifluoroethyl group, pentafluoroethyl group, 3,3,3-trifluoropropyl group, perfluoro-n-propyl group, fluoropropyl group, perfluoroisopropyl group, fluorobutyl group, 3,3,4,4,4-pentafluorobutyl group, perfluoro-n-butyl group, perfluoroisobutyl group, perfluoro-t-butyl group, perfluoro-sec-butyl group, fluoropentyl group, perfluoropentyl group, perfluoroisopentyl group, perfluoro-t-pentyl group, fluorohexyl group, perfluoro-n-hexyl group and perfluoroisohexyl group. Among these groups, a trifluoromethyl group, pentafluoroethyl group or perfluoro-n-propyl group is preferable, and a trifluoromethyl group or pentafluoroethyl group is more preferable.

Specific examples of the compound [I] include ammonium di(fluorosulfonyl)imide, ammonium N-(fluorosulfonyl)-N-(trifluoromethylsulfonyl)imide, ammonium N-(fluorosulfonyl)-N-(pentafluoroethylsulfonyl)imide, and ammonium N-(fluorosulfonyl)-N-(perfluoro-n-propylsulfonyl)imide; as well as cyclic fluoroalkanebis(sulfonyl)imide ammonium salts such as ammonium cyclodifluoromethanebis(sulfonyl)imide, ammonium cyclotetrafluoroethanebis(sulfonyl)imide (alternative name: ammonium 4,4,5,5-tetrafluoro-1,3,2-dithiazolidine-1,1,3,3-tetraoxide), and ammonium cyclohexafluoropropanebis(sulfonyl)imide (alternative name: ammonium 4,4,5,5,6,6-hexafluoro-1,3,2-dithiazinane-1,1,3,3-tetraoxide). Among these compounds, ammonium di(fluorosulfonyl)imide is preferable.

There are no particular limitations on the process used for producing the compound [I]. The compound [I] may be a commercially available product, or may be produced using the process disclosed in Japanese Unexamined Patent Application, First Publication No. 2010-168249.

There are no particular limitations on the metal hydroxide used in the cation exchange reaction, provided the metal hydroxide reacts with the compound [I] and undergoes cation exchange, but an alkali metal hydroxide is preferable. Examples of the alkali metal hydroxide include lithium hydroxide, sodium hydroxide, potassium hydroxide, rubidium hydroxide and cesium hydroxide. Of these, lithium hydroxide, sodium hydroxide or potassium hydroxide is preferable. These compounds may exist as hydrates.

The onium hydroxide used in the cation exchange reaction is a substance composed of an onium cation and a hydroxide anion. Examples of the onium hydroxide include imidazolium hydroxides such as 1,3-dimethylimidazolium hydroxide, 1-ethyl-3-methylimidazolium hydroxide, 1-butyl-3-methylimidazolium hydroxide, 1-hexyl-3-methylimidazolium hydroxide, 1-octyl-3-methylimidazolium hydroxide, 1-allyl-3-ethylimidazolium hydroxide, 1-allyl-3-butylimidazolium hydroxide, 1,3-diallylimidazolium hydroxide, 1-ethyl-2,3-dimethylimidazolium hydroxide, 1-butyl-2,3-dimethylimidazolium hydroxide, and 1-hexyl-2,3-dimethylimidazolium hydroxide;

pyrazolium hydroxides such as 2-ethyl-1,3,5-trimethylpyrazolium hydroxide, 2-propyl-1,3,5-trimethylpyrazolium hydroxide, 2-butyl-1,3,5-trimethylpyrazolium hydroxide, and 2-hexyl-1,3,5-trimethylpyrazolium hydroxide;

pyridinium hydroxides such as 1-ethylpyridinium hydroxide, 1-butylpyridinium hydroxide, 1-hexylpyridinium hydroxide, 1-octylpyridinium hydroxide, 1-ethyl-3-methylpyridinium hydroxide, 1-ethyl-3-hydroxymethylpyridinium hydroxide, 1-butyl-3-methylpyridinium hydroxide, 1-butyl-4-methylpyridinium hydroxide, 1-octyl-4-methylpyridinium hydroxide, 1-butyl-3,4-dimethylpyridinium hydroxide, and 1-butyl-3,5-dimethylpyridinium hydroxide;

pyrrolidinium hydroxides such as 1-propyl-1-methylpyrrolidinium hydroxide, 1-butyl-1-methylpyrrolidinium hydroxide, 1-hexyl-1-methylpyrrolidinium hydroxide, 1-octyl-1-methylpyrrolidinium hydroxide, and 1-butyl-1-propylpyrrolidinium hydroxide;

piperidinium hydroxides such as 1-propyl-1-methylpiperidinium hydroxide, 1-butyl-1-methylpiperidinium hydroxide, and 1-(2-methoxyethyl)-1-methylpiperidinium hydroxide;

morpholinium hydroxides such as 4-propyl-4-methylmorpholinium hydroxide and 4-(2-methoxyethyl)-4-methylmorpholinium hydroxide;

quaternary ammonium hydroxides such as tetramethylammonium hydroxide, tetraethylammonium hydroxide, tetrapropylammonium hydroxide, tetrabutylammonium hydroxide, tetraheptylammonium hydroxide, tetrahexylammonium hydroxide, tetraoctylammonium hydroxide, triethylmethylammonium hydroxide, propyltrimethylammonium hydroxide, diethyl-2-methoxyethylmethylammonium hydroxide, methyltrioctylammonium hydroxide, cyclohexyltrimethylammonium hydroxide, 2-hydroxyethyltrimethylammonium hydroxide, trimethylphenylammonium hydroxide, benzyltrimethylammonium hydroxide, benzyltributylammonium hydroxide, benzyltriethylammonium hydroxide, dimethyldistearylammonium hydroxide, diallyldimethylammonium hydroxide, 2-methoxyethoxymethyltrimethylammonium hydroxide, tetrakis(pentafluoroethyl)ammonium hydroxide, N-methoxytrimethyl ammonium hydroxide, N-ethoxytrimethylammonium hydroxide, and N-propoxytrimethylammonium hydroxide;

phosphonium hydroxides such as trihexyltetradecylphosphonium hydroxide;

sulfonium hydroxides such as trimethylsulfonium hydroxide;

guanidinium hydroxides such as guanidinium hydroxide and 2-ethyl-1,1,3,3-tetramethylguanidinium hydroxide;

isouronium hydroxides such as 2-ethyl-1,1,3,3-tetramethylisouronium hydroxide; and isothiouronium hydroxides such as 2-ethyl-1,1,3,3-tetramethylisothiouronium hydroxide.

By using these alkali metal hydroxides or onium hydroxides, ammonia is generated as a by-product in the cation exchange reaction. By performing the reaction while this ammonia is removed under reduced pressure, the equilibrium can be tilted to a state that promotes the cation exchange reaction.

The amount used of the metal hydroxide or the onium hydroxide can be adjusted appropriately in accordance with the average valency of the cation derived from the hydroxide. Specifically, the amount of the metal hydroxide or onium hydroxide is preferably within a range from 1 g equivalent to 10 g equivalent, and more preferably from 1 g equivalent to 5 g equivalent, per 1 g equivalent of the compound [I]. When only an alkali metal hydroxide is used, the amount of the alkali metal hydroxide is preferably from 1 mol to 10 mol, and more preferably from 1 mol to 5 mol, per 1 mol of the compound [I]. When only an alkali metal hydroxide is used, the amount of the onium hydroxide varies depending on the valency of the onium cation, but is preferably from 0.3 mol to 10 mol, and more preferably from 0.3 mol to 5 mol, per 1 mol of the compound [I].

The cation exchange reaction in the present invention can be performed in the presence of a solvent.

There are no particular limitations on the solvent. Examples of the solvent include water, alcohol-based solvents such as methanol, ethanol, n-propanol, i-propanol and n-butanol, ether-based solvents such as dioxane, 1,2-dimethoxyethane, tetrahydrofuran and ethylene glycol dimethyl ether, aromatic hydrocarbon solvents such as toluene, benzene and xylene, aliphatic hydrocarbon solvents such as n-pentane, n-hexane and n-heptane, halogenated hydrocarbon solvents such as dichloromethane, chloroform, carbon tetrachloride and 1,2-dichloroethane, amide-based solvents such as N,N-dimethylformamide, N,N-dimethylacetamide and N-methylpyrrolidone, nitrile-based solvents such as acetonitrile and benzonitrile, ester-based solvents such as ethyl acetate, isopropyl acetate and butyl acetate, and mixed solvents containing two or more of the above solvents. Of these solvents, from the viewpoint of workability during refining, a solvent that forms a two-layer state with water is preferable. Specifically, ethyl acetate, isopropyl acetate and butyl acetate are particularly preferable.

The temperature during the cation exchange reaction is preferably lower than the boiling point of the solvent at normal pressure. Specifically, the temperature during the cation exchange reaction is preferably within a range from 0° C. to 200° C., more preferably from 0° C. to 100° C., still more preferably from 10° C. to 100° C., and particularly preferably from 10° C. to 60° C. The time required for the reaction varies depending on the reaction scale, but is preferably from 0.1 hours to 48 hours, and more preferably from 0.5 hours to 24 hours.

The cation exchange reaction is performed under reduced pressure. By performing the reaction under reduced pressure, the ammonia that is generated as a by-product of the cation exchange reaction is removed, which tilts the equilibrium and enables the target product to be synthesized with good efficiency. The degree of vacuum is preferably set to a value that causes the solvent to reflux under the temperature mentioned above.

There are no particular limitations on the pressure during the reaction, provided it is a pressure lower than atmospheric pressure, but a pressure that is 10 torr or more lower than atmospheric pressure is preferable, a pressure that is 100 torr or more lower than atmospheric pressure is more preferable, and a pressure that is 300 torr or more lower than atmospheric pressure is still more preferable. The lower limit for the pressure depends on the vapor pressure of the solvent, but is preferably 0.01 torr, and more preferably 10 torr.

By performing the cation exchange reaction described above, a compound [II] can be obtained. The compound [II] is a fluorine-containing sulfonylimide salt represented by formula [II].

[Chemical Formula 4]

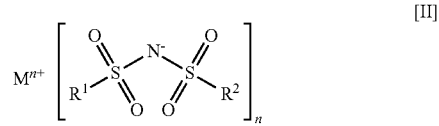

[II]

In formula [II], $M^{n+}$ represents a metal cation or an onium cation (excluding $NH_4^+$), n corresponds with the valency of the metal cation or the onium cation (excluding $NH_4^+$) and is an integer of 1 to 4 (and preferably an integer of 1 to 3), and $R^1$ and $R^2$ are the same as defined above in formula [I]. $R^1$ and $R^2$ may be bonded to each other to form a ring.

Although there are no particular limitations on the metal cation, an alkali metal cation is preferable. Examples of the alkali metal cation include a lithium cation, sodium cation, potassium cation, rubidium cation and cesium cation. Of these, a lithium cation, sodium cation or potassium cation is preferable.

Examples of the onium cation (excluding $NH_4^+$) include imidazolium cations such as a 1,3-dimethylimidazolium cation, 1-ethyl-3-methylimidazolium cation, 1-butyl-3-methylimidazolium cation, 1-hexyl-3-methylimidazolium cation, 1-octyl-3-methylimidazolium cation, 1-allyl-3-ethylimidazolium cation, 1-allyl-3-butylimidazolium cation, 1,3-diallylimidazolium hydroxide, 1-ethyl-2,3-dimethylimidazolium cation, 1-butyl-2,3-dimethylimidazolium cation, and 1-hexyl-2,3-dimethylimidazolium cation;

pyrazolium cations such as a 2-ethyl-1,3,5-trimethylpyrazolium cation, 2-propyl-1,3,5-trimethylpyrazolium cation, 2-butyl-1,3,5-trimethylpyrazolium cation, and 2-hexyl-1,3,5-trimethylpyrazolium cation;

pyridinium cations such as a 1-ethylpyridinium cation, 1-butylpyridinium cation, 1-hexylpyridinium cation, 1-octylpyridinium cation, 1-ethyl-3-methylpyridinium cation, 1-ethyl-3-hydroxymethylpyridinium cation, 1-butyl-3-methylpyridinium cation, 1-butyl-4-methylpyridinium cation, 1-octyl-4-methylpyridinium cation, 1-butyl-3,4-dimethylpyridinium cation, and 1-butyl-3,5-dimethylpyridinium cation;

pyrrolidinium cations such as a 1-propyl-1-methylpyrrolidinium cation, 1-butyl-1-methylpyrrolidinium cation, 1-hexyl-1-methylpyrrolidinium cation, 1-octyl-1-methylpyrrolidinium cation, and 1-butyl-1-propylpyrrolidinium cation;

piperidinium cations such as a 1-propyl-1-methylpiperidinium cation, 1-butyl-1-methylpiperidinium cation, and 1-(2-methoxyethyl)-1-methylpiperidinium cation;

morpholinium cations such as a 4-propyl-4-methylmorpholinium cation and 4-(2-methoxyethyl)-4-methylmorpholinium cation;

quaternary ammonium cations such as a tetramethylammonium cation, tetraethylammonium cation, tetrapropylammonium cation, tetrabutylammonium cation, tetraheptylammonium cation, tetrahexylammonium cation, tetraoctylammonium cation, triethylmethylammonium cation, propyltrimethylammonium cation, diethyl-2-methoxyethylmethylammonium cation, methyltrioctylammonium cation, cyclohexyltrimethylammonium cation, 2-hydroxyethyltrimethylammonium cation, trimethylphenylammonium cation, benzyltrimethylammonium cation, benzyltributylammonium cation, benzyltriethylammonium cation, dimethyldistearylammonium cation, diallyldimethylammonium cation, 2-methoxyethoxymethyltrimethylammonium cation, tetrakis(pentafluoroethyl)ammonium cation, N-methoxytrimethylammonium cation, N-ethoxytrimethylammonium cation, and N-propoxytrimethylammonium cation;

phosphonium cations such as a trihexyltetradecylphosphonium cation;

sulfonium cations such as a trimethylsulfonium cation;

guanidinium cations such as a guanidinium cation and 2-ethyl-1,1,3,3-tetramethylguanidinium cation;

isouronium cations such as a 2-ethyl-1,1,3,3-tetramethylisouronium cation; and isothiouronium cations such as a 2-ethyl-1,1,3,3-tetramethylisothiouronium cation.

Specific examples of the compound [II] include lithium salt compounds such as lithium di(fluorosulfonyl)imide, lithium N-(fluorosulfonyl)-N-(trifluoromethylsulfonyl)imide, lithium N-(fluorosulfonyl)-N-(pentafluoroethylsulfonyl)imide, lithium N-(fluorosulfonyl)-N-(perfluoro-n-propylsulfonyl)imide, lithium 4,4,5,5-tetrafluoro-1,3,2-dithiazolidine-1,1,3,3-tetraoxide, and lithium 4,4,5,5,6,6-hexafluoro-1,3,2-dithiazinane-1,1,3,3-tetraoxide;

potassium salt compounds such as potassium di(fluorosulfonyl)imide, potassium N-(fluorosulfonyl)-N-(trifluoromethylsulfonyl)imide, potassium N-(fluorosulfonyl)-N-(pentafluoroethylsulfonyl)imide, and potassium N-(fluorosulfonyl)-N-(perfluoro-n-propylsulfonyl)imide;

sodium salt compounds such as sodium di(fluorosulfonyl)imide, sodium N-(fluorosulfonyl)-N-(trifluoromethylsulfonyl)imide, sodium N-(fluorosulfonyl)-N-(pentafluoroethylsulfonyl)imide, and sodium N-(fluorosulfonyl)-N-(perfluoro-n-propylsulfonyl)imide;

imidazolium salt compounds such as 1,3-dimethylimidazolium di(fluorosulfonyl)imide, 1,3-dimethylimidazolium N-(fluorosulfonyl)-N-(trifluoromethylsulfonyl)imide, 1,3-dimethylimidazolium N-(fluorosulfonyl)-N-(pentafluoroethylsulfonyl)imide, and 1,3-dimethylimidazolium N-(fluorosulfonyl)-N-(perfluoro-n-propylsulfonyl)imide;

pyrazolium salt compounds such as pyrazolium di(fluorosulfonyl)imide, pyrazolium N-(fluorosulfonyl)-N-(trifluoromethylsulfonyl)imide, pyrazolium N-(fluorosulfonyl)-N-(pentafluoroethylsulfonyl)imide, and pyrazolium N-(fluorosulfonyl)-N-(perfluoro-n-propylsulfonyl)imide;

pyridinium salt compounds such as 1-ethylpyridinium di(fluorosulfonyl)imide, 1-ethylpyridinium N-(fluorosulfonyl)-N-(trifluoromethylsulfonyl)imide, 1-ethylpyridinium N-(fluorosulfonyl)-N-(pentafluoroethylsulfonyl)imide, and 1-ethylpyridinium N-(fluorosulfonyl)-N-(perfluoro-n-propylsulfonyl)imide;

pyrrolidinium salt compounds such as pyrrolidinium di(fluorosulfonyl)imide, pyrrolidinium N-(fluorosulfonyl)-N-(trifluoromethylsulfonyl)imide, pyrrolidinium N-(fluorosulfonyl)-N-(pentafluoroethylsulfonyl)imide, and pyrrolidinium N-(fluorosulfonyl)-N-(perfluoro-n-propylsulfonyl)imide;

piperidinium salt compounds such as 1-propyl-1-methylpiperidinium di(fluorosulfonyl)imide, 1-propyl-1-methylpiperidinium N-(fluorosulfonyl)-N-(trifluoromethylsulfonyl)imide, 1-propyl-1-methylpiperidinium N-(fluorosulfonyl)-N-(pentafluoroethylsulfonyl)imide, and 1-propyl-1-methylpiperidinium N-(fluorosulfonyl)-N-(perfluoro-n-propylsulfonyl)imide;

morpholinium salt compounds such as 4-propyl-4-methylmorpholinium di(fluorosulfonyl)imide, 4-propyl-4-methylmorpholinium N-(fluorosulfonyl)-N-(trifluoromethylsulfonyl)imide, 4-propyl-4-methylmorpholinium N-(fluorosulfonyl)-N-(pentafluoroethylsulfonyl)imide, and 4-propyl-4-methylmorpholinium N-(fluorosulfonyl)-N-(perfluoro-n-propylsulfonyl)imide;

quaternary ammonium salt compounds such as tetramethylammonium di(fluorosulfonyl)imide, tetramethylammonium N-(fluorosulfonyl)-N-(trifluoromethylsulfonyl)imide, tetramethylammonium N-(fluorosulfonyl)-N-(pentafluoroethylsulfonyl)imide, and tetramethylammonium N-(fluorosulfonyl)-N-(perfluoro-n-propylsulfonyl)imide;

phosphonium salt compounds such as trihexyltetradecylphosphonium di(fluorosulfonyl)imide, trihexyltetradecylphosphonium N-(fluorosulfonyl)-N-(trifluoromethylsulfonyl)imide, trihexyltetradecylphosphonium N-(fluorosulfonyl)-N-(pentafluoroethylsulfonyl)imide, and trihexyltetradecylphosphonium N-(fluorosulfonyl)-N-(perfluoro-n-propylsulfonyl)imide;

sulfonium salt compounds such as trimethylsulfonium di(fluorosulfonyl)imide, trimethylsulfonium N-(fluorosulfonyl)-N-(trifluoromethylsulfonyl)imide, trimethylsulfonium N-(fluorosulfonyl)-N-(pentafluoroethylsulfonyl)imide, and trimethylsulfonium N-(fluorosulfonyl)-N-(perfluoro-n-propylsulfonyl)imide;

guanidinium salt compounds such as guanidinium di(fluorosulfonyl)imide, guanidinium N-(fluorosulfonyl)-N-(trifluoromethylsulfonyl)imide, guanidinium N-(fluorosulfonyl)-N-(pentafluoroethylsulfonyl)imide, and guanidinium N-(fluorosulfonyl)-N-(perfluoro-n-propylsulfonyl)imide;

isouronium salt compounds such as 2-ethyl-1,1,3,3-tetramethylisouronium di(fluorosulfonyl)imide, 2-ethyl-1,1,3,3-tetramethylisouronium N-(fluorosulfonyl)-N-(trifluoromethylsulfonyl)imide, 2-ethyl-1,1,3,3-tetramethylisouronium N-(fluorosulfonyl)-N-(pentafluoroethylsulfonyl)imide, and 2-ethyl-1,1,3,3-tetramethylisouronium N-(fluorosulfonyl)-N-(perfluoro-n-propylsulfonyl)imide; and isothiouronium salt compounds such as 2-ethyl-1,1,3,3-tetramethylisothiouronium di(fluorosulfonyl)imide, 2-ethyl-1,1,3,3-tetramethylisothiouronium N-(fluorosulfonyl)-N-(trifluoromethylsulfonyl)imide, 2-ethyl-1,1,3,3-tetramethylisothiouronium N-(fluorosulfonyl)-N-(pentafluoroethylsulfonyl)imide, and 2-ethyl-1,1,3,3-tetramethylisothiouronium N-(fluorosulfonyl)-N-(perfluoro-n-propylsulfonyl)imide.

The compound [II] obtained in accordance with the production process of the present invention can be used favorably as a material for an ion conductor used in forming primary cells, secondary cells such as a lithium ion secondary cell, and electrochemical devices such as electrolytic capacitors, electrical double-layer capacitors, fuel cells, solar cells and electrochromic elements.

EXAMPLES

The present invention is described below in further detail based on a series of examples. However, the present invention is in no way limited by the following examples, and appropriate changes can, of course, be made while still conforming with the purport of the present invention, and such changes are all deemed to be included within the technical scope of the present invention.

Example 1

Synthesis of Potassium di(fluorosulfonyl)imide

A reaction vessel was charged with 6.2 g (23.5 mmol) of ammonium di(fluorosulfonyl)imide, 47 ml of butyl acetate, and a 20% aqueous solution containing 16.5 g (58.8 mmol) of potassium hydroxide, and the mixture was refluxed under an absolute pressure of 65 torr (approximately 8.669 kPa) and at a temperature of 37° C. for one hour. The reaction liquid was then cooled to 25° C. Subsequently, a liquid-liquid separation was performed, and the water phase was extracted 3 times with 24 ml samples of butyl acetate. The organic phases obtained in the extraction operations were combined, and the solvent was then removed from the organic phase by distillation under reduced pressure. Then, 39 ml of methylene chloride was added, and the mixture was stirred at 20° C. for 30 minutes. Subsequently, the crystals were collected by filtration. The thus obtained crystals were washed with 39 ml of methylene chloride, and were then dried at 20° C. under reduced pressure. Potassium di(fluorosulfonyl)imide was obtained in an amount of 4.6 g. The results of quantitative analysis by cation chromatography revealed that the entire product was composed of the potassium salt, and contained no ammonium ions, Example 2

Synthesis of Lithium di(fluorosulfonyl)imide

To 9.8 g (49.6 mmol) of ammonium di(fluorosulfonyl) imide were added 99 ml of butyl acetate, 6.2 g (148.8 mmol) of lithium hydroxide monohydrate and 37 ml of water, and the mixture was refluxed under an absolute pressure of 65 torr (approximately 8.669 kPa) and at a temperature of 37° C. for one hour. The reaction liquid was then cooled to 25° C. Subsequently, a liquid-liquid separation was performed, and the water phase was extracted 3 times with 50 ml samples of butyl acetate. The organic phases obtained in the extraction operations were combined, and then washed twice with 3 ml samples of water. Subsequently, the solvent was removed by distillation under reduced pressure. Then, 50 ml of methylene chloride was added, and the mixture was stirred at 20° C. for 19 hours. Subsequently, the crystals were collected by filtration. The thus obtained crystals were washed with 50 ml of methylene chloride, and were then dried at 20° C. under reduced pressure. Lithium di(fluorosulfonyl)imide was obtained in an amount of 4.5 g. The results of quantitative analysis by cation chromatography revealed that the entire product was composed of the lithium salt, and contained no ammonium ions.

Example 3

Synthesis of Sodium di(fluorosulfonyl)imide

To 4.9 g (24.7 mmol) of ammonium di(fluorosulfonyl) imide were added 49 ml of butyl acetate and a 20% aqueous solution containing 12.4 g (61.8 mmol) of sodium hydroxide, and the mixture was refluxed under an absolute pressure of 65 torr (approximately 8.669 kPa) and at a temperature of 37° C. for one hour. The reaction liquid was then cooled to 25° C. Subsequently, a liquid-liquid separation was performed, and the water phase was extracted 3 times with 25 ml samples of butyl acetate. The organic phases obtained in the extraction operations were combined, and the solvent was then removed from the organic phase by distillation under reduced pressure. Then, 41 ml of methylene chloride was added, and the mixture was stirred at 20° C. for 15 minutes. Subsequently, the crystals were collected by filtration. The thus obtained crystals were washed with 20 ml of methylene chloride, and were then dried at 20° C. under reduced pressure. Sodium di(fluorosulfonyl)imide was obtained in an amount of 3.5 g. The results of quantitative analysis by cation chromatography revealed that the entire product was composed of the sodium salt, and contained no ammonium ions.

Example 4

Synthesis of Ammonium di(fluorosulfonyl)imide

A reaction vessel made of a fluororesin was charged with 2.14 g (10.0 mmol) of di(chlorosulfonyl)imide. Then, 20 ml of ethyl acetate and 1.78 g (48.0 mmol) of $NH_4F$ were added to the vessel, and a reaction was performed under reflux at 75° C. for 4 hours. Following completion of the reaction, the reaction mixture was cooled to room temperature and washed with 2.5 ml of water to obtain ammonium di(fluorosulfonyl) imide.

Synthesis of Potassium di(fluorosulfonyl)imide

To the ethyl acetate solution of ammonium di(fluorosulfonyl)imide obtained in the manner described above was added a 10% aqueous solution containing 0.84 g (15.0 mmol) of potassium hydroxide, and the mixture was refluxed under an absolute pressure of 225 torr (approximately 29.997 kPa) and at a temperature of 40° C. for one hour. The reaction liquid was then cooled to 25° C. Subsequently, a liquid-liquid separation was performed, and the water phase was extracted twice with 20 ml samples of ethyl acetate. The organic phases obtained in the extraction operations were combined, and the solvent was then removed from the organic phase by distillation under reduced pressure. Potassium di(fluorosulfonyl) imide salt was obtained in an amount of 1.55 g. The results of quantitative analysis by cation chromatography revealed a molar ratio between the potassium salt and the ammonium salt of di(fluorosulfonyl)imide of 97:3.

Comparative Example 1

Synthesis of Potassium di(fluorosulfonyl)imide

A reaction vessel was charged with 0.90 g (4.6 mmol) of ammonium di(fluorosulfonyl)imide, 10 ml of butyl acetate, and a 10% aqueous solution containing 0.40 g (7.2 mmol) of potassium hydroxide, and the mixture was stirred for one hour at atmospheric pressure (approximately 101.325 kPa) and a temperature of 20° C. Subsequently, a liquid-liquid separation was performed, and the water phase was extracted twice with 10 ml samples of butyl acetate. The organic phases obtained in the extraction operations were combined, and the solvent was then removed from the organic phase by distillation under reduced pressure. A di(fluorosulfonyl)imide salt was obtained in an amount of 0.66 g. The results of quantitative analysis by cation chromatography revealed a molar ratio between the potassium salt and the ammonium salt of di(fluorosulfonyl)imide of 91:9.

Comparative Example 2

Synthesis of Ammonium di(fluorosulfonyl)imide

A reaction vessel made of a fluororesin was charged with 2.14 g (10.0 mmol) of di(chlorosulfonyl)imide. Then, 20 ml of ethyl acetate and 1.78 g (48.0 mmol) of NH$_4$F were added to the vessel, and a reaction was performed under reflux at 75° C. for 4 hours. Following completion of the reaction, the reaction mixture was cooled to room temperature and washed with 2.5 ml of water to obtain ammonium di(fluorosulfonyl)imide.

Synthesis of Potassium di(fluorosulfonyl)imide

To the ethyl acetate solution of ammonium di(fluorosulfonyl)imide obtained in the manner described above was added a 10% aqueous solution containing 0.84 g (15.0 mmol) of potassium hydroxide, and the mixture was refluxed under heat at atmospheric pressure (approximately 101.325 kPa) and a temperature of 40° C. for one hour. The reaction liquid was then cooled to 25° C. Subsequently, a liquid-liquid separation was performed, and the water phase was extracted twice with 20 ml samples of ethyl acetate. The organic phases obtained in the extraction operations were combined, and the solvent was then removed from the organic phase by distillation under reduced pressure. Potassium di(fluorosulfonyl)imide salt was obtained in an amount of 1.38 g. The results of quantitative analysis by cation chromatography revealed a molar ratio between the potassium salt and the ammonium salt of di(fluorosulfonyl)imide of 84:16.

INDUSTRIAL APPLICABILITY

According to the present invention, a fluorine-containing sulfonylimide alkali metal salt or a fluorine-containing sulfonylimide onium salt (excluding the ammonium salt) can be produced from a fluorine-containing sulfonylimide ammonium salt in an industrially efficient manner.

The invention claimed is:

1. A process for producing a fluorine-containing sulfonylimide salt of the following formula [II], the process comprising subjecting a fluorine-containing sulfonylimide ammonium salt of the following formula [I] to a cation exchange reaction under a reduced pressure of 0.01 to 65 torr in the presence of a solvent, using at least one compound selected from the group consisting of metal hydroxides and onium hydroxides:

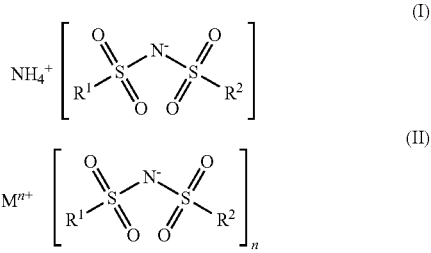

wherein in formula [I] and formula [II]:
  each of R$^1$ and R$^2$ independently is a fluoroalkyl group having 1 to 6 carbon atoms or a fluorine atom, and
  R$^1$ and R$^2$ may be bonded to each other to form a ring; and
  wherein in formula [II]:
  M$^{n+}$ is a metal cation or an onium cation (excluding NH$_4^+$), and
  n is the valency of the metal cation or the onium cation (excluding NH$_4^+$), wherein n is an integer of 1 to 4,
  wherein the solvent is butyl acetate, and
  wherein the cation exchange reaction product does not contain ammonium ions.

2. The process for producing a fluorine-containing sulfonylimide salt according to claim 1, wherein the at least one compound is selected from the group consisting of alkali metal hydroxides and onium hydroxides.

* * * * *